US009494599B2

(12) United States Patent
Rautou et al.

(10) Patent No.: US 9,494,599 B2
(45) Date of Patent: Nov. 15, 2016

(54) METHODS AND KITS FOR DETERMINING WHETHER A PATIENT WITH CIRRHOSIS IS AT RISK OF HAVING CLINICALLY SIGNIFICANT PORTAL HYPERTENSION

(71) Applicants: INSERM (INSTITUT NATIONAL DE LA SANTE ET DE LA RECHERCHE MEDICALE), Paris (FR); UNIVERSITE PARIS DIDEROT (PARIS VII), Paris (FR); UNIVERSITE DE VERSAILLES SAINT-QUENTIN-EN-YVELINES, Versailles (FR); UNIVERSITE PARIS DESCARTES, Paris (FR); ASSISTANCE PUBLIQUE-HOPITAUX DE PARIS, Paris (FR)

(72) Inventors: Pierre-Emmanuel Rautou, Paris (FR); Chantal Boulanger, Paris (FR); Dominique-Charles Valla, Paris (FR)

(73) Assignees: INSERM (INSTITUT NATIONAL DE LA SANTE ET DE LA RECHERCHE MEDICALE), Paris (FR); UNIVERSITE PARIS DIDEROT (PARIS VII), Paris (FR); UNIVERSITE DE VERSAILLES SAINT-QUENTIN-EN-YVELINES, Versailles (FR); UNIVERSITE PARIS DESCARTES, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 14/374,243

(22) PCT Filed: Jan. 28, 2013

(86) PCT No.: PCT/EP2013/051566
§ 371 (c)(1),
(2) Date: Jul. 24, 2014

(87) PCT Pub. No.: WO2013/110808
PCT Pub. Date: Aug. 1, 2013

(65) Prior Publication Data
US 2015/0168426 A1 Jun. 18, 2015

(30) Foreign Application Priority Data

Jan. 27, 2012 (EP) ..................... 12152833

(51) Int. Cl.
G01N 33/68 (2006.01)
G01N 33/569 (2006.01)

(52) U.S. Cl.
CPC .... *G01N 33/6893* (2013.01); *G01N 33/56966* (2013.01); *G01N 2333/4742* (2013.01);
(Continued)

(58) Field of Classification Search
CPC ................... G01N 33/6893; G01N 33/56966; G01N 33/4742; G01N 33/70596; G01N 33/70503; G01N 33/70514; G01N 33/70553
See application file for complete search history.

(56) References Cited

FOREIGN PATENT DOCUMENTS

WO 2007/136674 11/2007

OTHER PUBLICATIONS

Rautou et al. Abnormal Plasma Microparticles Impair Vasoconstrictor Responses in Patients with Cirrhosis. Gastroenterology 143: 166-176 (Jan. 1, 2012).*

(Continued)

*Primary Examiner* — Gail R Gabel
(74) *Attorney, Agent, or Firm* — Whitham, Curtis & Cook, P.C.

(57) ABSTRACT

The present invention relates to a method for determining whether a patient with cirrhosis is at risk of having clinically significant portal hypertension comprising the steps consisting of i) quantifying the levels of leuko-endothelial (CD31+/41−), pan-leukocyte (CD11a+), lymphocyte (CD4+), erythrocyte (CD235a+) and hepatocyte-derived (cytokeratin-18+) microparticles in a blood sample obtained from the patient and ii) comparing said levels with predetermined reference values wherein a difference between the levels quantified at step i) and the predetermined reference values is indicative whether the patient is at risk of having clinically significant portal hypertension.

12 Claims, 8 Drawing Sheets

(52) U.S. Cl.
CPC .............. *G01N2333/70503* (2013.01); *G01N 2333/70514* (2013.01); *G01N 2333/70553* (2013.01); *G01N 2333/70596* (2013.01); *G01N 2800/085* (2013.01)

(56) References Cited

OTHER PUBLICATIONS

Amabile et al. Circulating Endothelial Microparticles Are Associated with Vascular Dysfunction in Patients with End-Stage Renal Failure. J Am Soc Nephrol 16: 3381-3388 (2005).*

Bakouboula et al. Procoagulant Membrane Microparticles Correlate with the Severity of Pulmonary Arterial Hypertension. Am J Respit Ctri Care Med 177: 536-543 (2008).*

Kornek et al. Human T Cell Microparticles Circulate in Blood of Hepatitis Patients and Induce Fibrolytic Activation of Hepatic Stellate Cells. Hepatology 53: 230-242 (2011).*

Brodsky et al., "Dynamics of Circulating Microparticles in Liver Transplant Patients", J Gastrointestin Liver Dis, Sep. 1, 2008, pp. 261-268.

Bakouboula et al., "Procoagulant Membrane Microparticles Correlate with the Severity of Pulmonary Arterial Hypertension", American Journal of Respiratory and Critical Care Medicine, Jan. 1, 2007, pp. 536-543, vol. 177, No. 5.

La Mura et al., "Von Willebrand factor levels predict clinical outcome in patients with cirrhosis and portal hypertension", Gut, Aug. 2011, pp. 1133-1138, vol. 60, No. 8.

Westerhoff et al., "CD61, CD31, and CD34 improve diagnostic accuracy in gastric antral vascular ectasia and portal hypertensive gastropathy: an immunohistochemical and digital morphometric study", The American Journal of Surgical Pathology, Apr. 2010, pp. 494-501, vol. 34, No. 4.

Amabile et al., "Circulating Endothelial Microparticles Are Associated with Vascular Dysfuntion in Patients with End-Stage Renal Failure", Journal of the American Society of Nephrology, Nov. 1, 2005, pp. 3381-3388, vol. 16, No. 11, Williams and Wilkins.

Rautou, P., "Circulating microparticles from cirrhotic patients impair vasoconstriction", The Liver Meeting, Sep. 2, 2010, Web.

Miroslaw et al., "Human T cell microparticles circulate in blood of hepatitis patients and induce fibrolytic activation of hepatic stellate cells", Hepatology, Jan. 1, 2011, pp. 230-242, vol. 53, No. 1.

Pfeffel et al., "Soluble CD8 and soluble CD4 antigens in viral hepatitis and alcoholic cirrhosis", Journal of Hepatology, Feb. 1, 1994, pp. 245-251, vol. 20, No. 2.

Rautou et al., "Abnormal Plasma Microparticles Impair Vasoconstrictor Responses in Patients with Cirrhosis", Gastroenterology, Jan. 1, 2012, pp. 1-17, Elsevier, Philadelphia, PA.

* cited by examiner

METHODS AND KITS FOR DETERMINING WHETHER A PATIENT WITH CIRRHOSIS IS AT RISK OF HAVING CLINICALLY SIGNIFICANT PORTAL HYPERTENSION

FIELD OF THE INVENTION

The present invention relates to methods and kits for determining whether a patient with cirrhosis is at risk of having clinically significant portal hypertension.

BACKGROUND OF THE INVENTION

In cirrhosis, abnormal persistent vasodilation of arterial vessels leads to increased portal venous inflow and contributes to portal hypertension. Indeed, portal hypertension is determined by both the degree of hepatic outflow resistance, related to liver architecture changes, and the extent of inflow into the portal venous system from the splanchnic bed. Portal hypertension is a major factor in the development of complications of cirrhosis, and as arterial vasodilation associated with portal hypertension is potentially reversible, understanding its mechanisms is of great therapeutic interest[1]. The gold-standard for assessing portal hypertension is currently hepatic venous pressure gradient measurement. However, this technique is invasive and available only in expert centres. Thus, there is a strong need for developing non-invasive techniques to help physicians for determining whether a patient with cirrhosis is at risk of having clinically significant portal hypertension (de Franchis, Journal of Hepatology 2010 vol. 53 j 762-768).

Vasodilation is associated with both enhanced formation of vasodilators, and vascular hyporesponsiveness to vasoconstrictors, also referred as to "vascular hypocontractility". Nitric oxide (NO) overproduction cannot fully account for this effect, and several studies including those in endothelial nitric oxide synthase (NOS-3) knockout mice have shown that other factors are involved in the pathogenesis of arterial vasodilation. However, little is known about these factors, and more importantly, the mechanisms leading to vascular hypocontractility have not yet been elucidated[1].

Microparticles (MPs) are membrane vesicles with a diameter ranging from 0.1 to 1 μm, released in extracellular space following cell activation or apoptosis[2]. MPs harbor at their surface most of the membrane-associated proteins of the cells they stem from and are characterized by the loss of plasma membrane asymmetry resulting in the exposure of phosphatidylserine on their outer leaflet[2]. MPs are present in the blood of healthy subjects and their levels are increased in patients with high atherothrombotic risk[2]. MPs are not inert by-products. A number of studies point out that MPs can affect several cellular functions, including vascular tone and vascular reactivity[2]. However, these studies were performed using MPs generated in vitro or isolated from patients with cardiovascular diseases or sepsis[2].

SUMMARY OF THE INVENTION

The present invention relates to a method for determining whether a patient with cirrhosis is at risk of having clinically significant portal hypertension comprising the steps consisting of i) quantifying the levels of leuko-endothelial (CD31+/41−), pan-leukocyte (CD11a+), lymphocyte (CD4+), erythrocyte (CD235a+) and hepatocyte-derived (cytokeratin-18+) microparticles in a blood sample obtained from the patient and ii) comparing said levels with predetermined reference values wherein a difference between the levels quantified at step i) and the predetermined reference values is indicative whether the patient is at risk of having clinically significant portal hypertension.

DETAILED DESCRIPTION OF THE INVENTION

Circulating membrane-shed microparticles (MPs) have been shown to participate in the regulation of vascular tone. The inventors aimed to evaluate the cellular origin of plasma MPs in patients with cirrhosis and assess their potential contribution to arterial vasodilation, a crucial mechanism of portal hypertension. Thus the inventors isolated MPs from the blood of 91 patients with cirrhosis and 30 healthy controls. MP level and origin were analyzed using flow cytometry and their effects on the vascular response to vasoconstrictors were examined both in vitro and in vivo. Circulating levels of leuko-endothelial (CD31+/41−), pan-leukocyte (CD11a+), lymphocyte (CD4+) and erythrocyte (CD235a+) MPs were higher in patients with cirrhosis than in controls. Plasma of patients with cirrhosis contained hepatocyte-derived (cytokeratin-18+) MPs, while plasma from controls did not. Cirrhosis severity and systemic inflammation were major determinants of leuko-endothelial and hepatocyte MP levels. MPs from patients with advanced cirrhosis significantly impaired contraction to phenylephrine, whereas MPs from healthy controls or from Child-Pugh A patients did not. This effect was dependent on cyclo-oxygenase-type1 and required the presence of phosphatidylserine externalized at the surface of MPs, which was transferred to endothelial cells and acted as substrate for phospholipase A2 production of arachidonic acid metabolites. Intravenous injection of human cirrhotic MPs decreased mean arterial blood pressure in healthy mice. The inventors concluded that cirrhosis is associated with an increase in several circulating MP subpopulations, likely resulting from systemic inflammation and liver cell damage. Plasma MPs from patients with advanced cirrhosis impair vasoconstrictor responses and blood pressure, contributing therefore to arterial vasodilation associated with portal hypertension.

Accordingly a first object of the invention relates to a method for determining whether a patient with cirrhosis is at risk of having clinically significant portal hypertension comprising the steps consisting of i) quantifying the levels of leuko-endothelial (CD31+/41−), pan-leukocyte (CD11a+), lymphocyte (CD4+), erythrocyte (CD235a+) and hepatocyte-derived (cytokeratin-18+) microparticles in a blood sample obtained from the patient and ii) comparing said levels with predetermined reference values wherein a difference between the levels quantified at step i) and the predetermined reference values is indicative whether the patient is at risk of having clinically significant portal hypertension.

As used herein the term "significant portal hypertension" has its general meaning in the art and refer to a hepatic venous pressure gradient≥10 mmHg) (de Franchis, J Hepatol 2010).

The term "blood sample" means a whole blood, serum, or plasma sample obtained from the patient. Preferably the blood sample, according to the invention, is a plasma sample. A plasma sample may be obtained using methods well known in the art. For example, blood may be drawn from the patient following standard venipuncture procedure on tri-sodium citrate buffer. Plasma may then be obtained from the blood sample following standard procedures including but not limited to, centrifuging the blood sample at about 500*g for about 15-20 minutes (room temperature), followed by pipeting of the plasma layer. Platelet-free plasma (PFP) will be obtained following centrifugation at about 15,000*g for 5 min. Analyses can be performed directly on this PFP. Alternatively, MPs may be more specifically isolated by further centrifuging the PFP at about 15,000 to about 25,000*g at 4° C. Different buffers may be considered appropriate for resuspending the pelleted cellular debris which contains the MPs. Such buffers include reagent grade (distilled or deionized) water and phosphate buffered saline (PBS) pH 7.4. Preferably, PBS buffer (Sheath fluid) is used.

"Risk" in the context of the present invention, relates to the probability that an event will occur over a specific time period, as in the conversion to clinically significant portal hypertension, and can mean a patient's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a patient compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion.

As used herein the term "microparticle" or "MP" has its general meaning in the art and denotes a plasma membrane vesicle shed from an apoptotic or activated cell. The size of microparticles ranges from 0.1 µm to 1 µm in diameter. The surface markers of microparticles are the same as the cells from they originated. Accordingly leuko-endothelial microparticles express CD31 and not CD41. Pan-leukocyte microparticles express CD11a+. Lymphocyte microparticle express CD4. Erythrocyte microparticles express CD235a. Hepatocyte-derived microparticles express cytokeratin-18+.

Standard methods for isolating microparticles are well known in the art. For example the methods may consist in collecting a population of microparticles from a patient and using differential binding partners directed against the specific surface markers of said microparticles, wherein microparticles are bound by said binding partners to said surface markers.

In a particular embodiment, the methods of the invention comprise contacting the blood sample with a set of binding partners capable of selectively interacting with microparticles present in the blood sample. The binding partner may be an antibody that may be polyclonal or monoclonal, preferably monoclonal, directed against the specific surface marker of microparticles. In another embodiment, the binding partners may be a set of aptamers.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique; the human B-cell hybridoma technique; and the EBV-hybridoma technique.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A, that are selected from combinatorial libraries by two hybrid methods.

The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody or aptamer, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188. Preferably, the antibodies against the surface markers are already conjugated to a fluorophore (e.g. FITC-conjugated and/or PE-conjugated).

The aforementioned assays may involve the binding of the binding partners (i.e. antibodies or aptamers) to a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. The solid surfaces are preferably beads. Since microparticles have a diameter of roughly 0.1 to 1 µm, the beads for use in the present invention should have a diameter larger than 1 µm. Beads may be made of different materials, including but not limited to glass, plastic, polystyrene, and acrylic. In addition, the beads are preferably fluorescently labelled.

According to the invention, methods of flow cytometry are preferred methods for determining the level of microparticles in the blood sample obtained from the patient. For example, fluorescence activated cell sorting (FACS) may be therefore used to separate in the blood sample the desired microparticles. In another embodiment, magnetic beads may be used to isolate microparticles (MACS). For instance, beads labelled with monoclonal specific antibodies may be used for the positive selection of microparticles. Other methods can include the isolation of microparticles by depletion of non microparticles components (negative selection). For example, microparticles may be excited with 488 nm light and logarithmic green and red fluorescences of FITC and PE may be measured through 530/30 nm and 585/42 nm bandpass filters, respectively. The absolute number of microparticles may then be calculated through specific software useful in practicing the methods of the present invention. Typically, a fluorescence activated cell sorting (FACS) method such as described in Example 1 here below may be used to determine the levels of microparticles in the blood sample obtained from the patient. Accordingly, in a specific embodiment, the method of the invention comprises the steps of obtaining a blood sample as above described; putting said prepared sample into a container; adding both labeled antibodies against surface markers that are specific to microparticles of interest, and a known concentration of fluorescent solid surfaces; performing a FACS analysis on the prepared sample in order to calculate the absolute number of microparticles therein.

When flow cytometry may be not performed (for example for hepatocyte-derived (cytokeratin-18+) microparticles) an ELISA method can be used, wherein the wells of a microtiter plate are coated with a set of antibodies which recognize said the microparticle of interest. The blood sample is then added to the coated wells. After a period of incubation sufficient to allow the formation of antibody-antigen complexes, the plate(s) can be washed to remove unbound moieties and a detectably labelled secondary binding molecule is added. The secondary binding molecule is allowed to react with any captured sample marker protein, the plate washed and the presence of the secondary binding molecule detected using methods well known in the art. Typically an ELISA method for quantifying the level of hepatocyte-derived (cytokeratin-18+) microparticles is described in example 1 below.

In one embodiment, the predetermined reference values may be index values or may be derived from one or more risk prediction algorithms or computed indices for clinically significant portal hypertension event. A reference value can be relative to a number or value derived from population studies, including without limitation, such patients having similar body mass index, total cholesterol levels, LDL/HDL levels, systolic or diastolic blood pressure, patients of the same or similar age range, patients in the same or similar ethnic group, and patients having the same severity of cirrhosis. Such predetermined reference values can be derived from statistical analyses and/or risk prediction data of populations obtained from mathematical algorithms and computed indices of clinically significant portal hypertension. In one embodiment of the present invention, the predetermined reference values are derived from the level of the microparticles of the invention in a control sample derived from one or more patients who were not subjected to clinically significant portal hypertension. Furthermore, retrospective measurement of the level of the microparticles in properly banked historical patient samples may be used in establishing these predetermined reference values. Typically, the levels of microparticles in a patient who is at risk of having clinically significant portal hypertension is deemed to be higher than the reference value obtained from the general population or from healthy patients. In some embodiments, a probability score is calculated, which is derived from running a model that include the levels for each microparticle of the invention and optionally various patient parameters (e.g., age, gender, weight, race, cirrhosis severity). The weight given to each microparticle of the invention and optionally to each parameter is based on its contribution relative to the other parameters in explaining the inter-individual variability for having clinically significant portal hypertension. In some embodiments, the score may be established by a computer program.

The method of the invention is thus particularly suitable for predicting clinical complications due to significant portal hypertension such as ascites. The result given by the methods of the invention may be used as a guide in selecting a therapy or treatment regimen for the patient. For example, when the patient has been determined as having a risk of having clinically significant portal hypertension he can be eligible for a preventive treatment (e.g. administration of B-blockers, vasoactive drugs) or even for liver transplantation.

Yet another object of the invention relates to a kit for performing the method of the invention comprising means for quantifying the levels of at least one leuko-endothelial (CD31+/41−), pan-leukocyte (CD11a+), lymphocyte (CD4+), erythrocyte (CD235a+) and hepatocyte-derived (cytokeratin-18+) microparticles in a blood sample obtained from said patient. The kit may include a set of antibodies as above described. In a particular embodiment, the antibody or set of antibodies are labelled as above described. The kit may also contain other suitably packaged reagents and materials needed for the particular detection protocol, including solid-phase matrices, if applicable, and standards.

The invention will be further illustrated by the following figures and examples. However, these examples and figures should not be interpreted in any way as limiting the scope of the present invention.

EXAMPLE 1

Figure 1A:
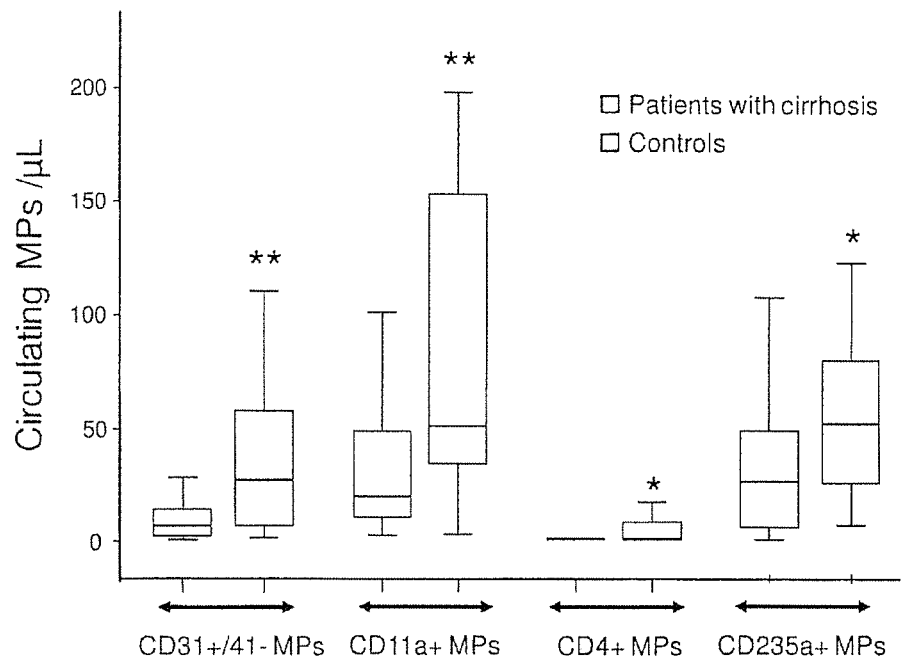
FIG. 1. Cellular origin of circulating MPs in patients with cirrhosis and in healthy controls. A. CD31+/41− CD11a+, CD4+ and CD235a+, MPs are of leuko-endothelial, pan-leukocyte, lymphocyte and erythrocyte origin, respectively (flow cytometry analysis; 26 patients with cirrhosis, 30 healthy controls). B. Soluble native cytokeratine 18 levels (M65 antigen), a marker of hepatocytes, in native and filtrated (to remove MPs) plasmas (ELISA assay; 9 patients with cirrhosis vs. 5 controls). The difference between native and filtrated M65 antigen level reflects the level of MPs derived from hepatocytes. C. Circulating levels of CD31+/41− in 91 patients with cirrhosis according to Child-Pugh score (A, n=16; B, n=18; C, n=55). D. Levels of cytokeratine 18 (M65 antigen) bound to MPs (obtained by the difference between native and filtrated M65 antigen level) according to Child-Pugh score (A, n=9; B, n=9; C, n=22). Data are given as median (horizontal bar), 25th and 75th percentile (boxes), and extreme values which are less than 3 box lengths from either end of the box (error bar). ns, not significant; *$p<0.05$; $p<0.01$; *, $p<0.001$.

Abnormal Plasma Microparticle Levels Impair Vasoconstrictor Responses in Cirrhosis Material & Methods
Patients and Controls
We included 91 patients admitted to the Liver Unit (Hôpital Beaujon, Clichy, France) for alcoholic and/or hepatitis C virus related cirrhosis during two periods of time: between 2007 and 2008, 26 patients (the pilot cohort); and between 2010 and 2011, 65 additional patients. None of the patients had severe sepsis, hepatocellular carcinoma assessed using serum alpha-fetoprotein level and CT-scan or ultrasonography, or portal vein thrombosis. The pilot cohort was compared to a group of 30 healthy volunteer subjects. All patients and controls gave their informed consent to participate to the study. The study conformed to the ethical guidelines of the 1975 declaration of Helsinki.

Isolation of Circulating MPs
Circulating MPs were isolated from platelet-free plasma obtained by successive centrifugations of venous blood as reported earlier[5]. Briefly, citrated venous blood (15 mL) was centrifuged at 500 g for 15 min to remove cells, then at 15200 g for 5 min to remove cell debris and apoptotic bodies (+18° C.)[5-6]. H-Gly-Pro-Arg-Pro-OH (Calbiochem, La Jolla, Calif., 5 µmol/L) was then added, and the samples were stored frozen at −80° C. until use.

Flow Cytometry Analysis of MPs
MPs were analyzed on a Coulter EPICS XL flow cytometer (Beckman Coulter, Villepinte, France) as previously described[1]. Regions corresponding to MPs were identified in forward light scatter (FSC) and side-angle light scatter (SSC) intensity dot plot representation set at logarithmic gain. MP gate was defined, using calibration beads (Megamix, Biocytex, France and 0.1 µm beads, Invitrogen, Eugene, Oreg.), as events with a 0.1 to 1 µm diameter and then plotted on a fluorescence/FSC fluorescence dot plot to determine MP counts positively labelled by specific antibodies. A known amount of Flowcount calibrator beads (Beckman Coulter, Fullerton, Calif.; 20 µL) was added to each sample just before performing flow cytometry analysis. MP concentration was assessed by comparison to these Flowcount calibrator beads. Presence of phosphatidylserine at the surface of plasma MPs was assessed using fluoroisothiocyanate-conjugated Annexin V (Roche Diagnostics, Mannheim, Germany) diluted in appropriate buffer (140 mmol/L NaCl, 10 mmol/L HEPES, pH 7.4) (Roche Diagnostics, Mannheim, Germany) in the presence or in the absence of $CaCl_2$ (5 mmol/L), as a negative control[1]. As previously described[1], cellular origin of plasma MPs was determined using selective fluorochrome-labelled antibodies or their corresponding isotype-matched immunoglobulin, incubated at room temperature for 30 minutes in the dark with 20 µL of platelet-free plasma. Anti-CD11a-Fluoroisothiocyanate was provided by Immunotech, Marseille, France. Anti-CD31-Phycoerythrin, anti-CD41-Phycoerythrin-Cyanin5, and anti-CD235a-Fluoroisothiocyanate were obtained from Beckman-Coulter (Villepinte, France). Anti-CD14-Phycoerythrin was provided by Caltag Laboratories (Burlingame, Calif.) and anti-CD4-Phycoerythrin by BD Pharmingen (San Jose, Calif.).

ELISA Assays
In order to assess hepatocyte-derived MP levels, native soluble cytokeratin-18 levels (M65-antigen) were determined by commercially available immunoassays (M65 ELISA kit, Peviva AB, Bromma, Sweden) in the plasma of controls and of patients both before and after two successive 0.2 µm filtrations (Ceveron MFU 500, Technoclone, Austria). The difference between soluble cytokeratin-18 levels in initial and in filtrated plasma reflected the concentration in hepatocyte MPs. The stable metabolite of PGI2, i.e. 6-keto PGF1α, was measured by enzyme immunoassays (Cayman chemical company, Ann Arbor, Mich.) in the medium of aortic rings incubated for 1 hour with MPs or the corresponding supernatant.

Organ Chamber Experiments
In order to obtain, after dilution in aortic ring medium or in endothelial cell medium, concentrations in MPs similar to those present in the plasma of the patients, circulating MPs were concentrated from platelet-free plasma using centrifugation at 20500 g for 150 minutes (+4° C.) and resuspended in a volume of Dulbecco's modified eagle medium (DMEM) corresponding to 1/10 of the initial volume of plasma. The effect of MPs was compared either to the effect of the same volume of platelet-free plasma devoid of MPs (i.e. the supernatant obtained after the 20500 g centrifugation and then filtered on 0.22 and 0.1 µm filters; thereafter referred to as "supernatant") also resuspended in DMEM or to the effect of DMEM alone.

Detailed description of organ chamber experiments is provided in Supplementary Methods. Briefly, rings from rat thoracic aortas were incubated with circulating MPs from patients or from controls at their circulating concentration, or with the 20500 g supernatant or with DMEM alone. After 24 hours, the rings were mounted in organ chambers filled with modified Krebs-Ringer solution to study relaxation to acetylcholine chloride and contraction to phenylephrine, as previously reported[7-8]. Pilot experiments indicated that plasma MP effect was similar at 2 and 24 hrs exposure (data not shown); therefore unless otherwise stated, all experiments were performed after 24 hrs incubation.

In one experiment, rings from human mesenteric artery branches, obtained from a liver transplantation donor and transferred in cold sterile DMEM supplemented with antibiotics (100 IU/mL Streptomycin, 100 IU/mL Penicillin and 10 µg/mL Polymyxin B; Sigma; St Louis, Mo.) were used.

Induction of Cirrhosis by Bile Duct Ligation

Cirrhosis was induced in male 12 weeks-old Wistar rats (Charles River Laboratories, Saint-Aubin-les-Elbeuf, France) by bile duct ligation, as described[9] (see Supplementary Methods for details).

Endothelial Cell Culture

Human umbilical vein endothelial cells (HUVEC) plated in 24 or 6-well plates and incubated at 37° C. in a 5% $CO_2$ incubator. HUVECs (2 different donors) were obtained from Promocell (Heidelberg, Germany) and cultured in endothelial cell basal medium supplemented with serum and growth factors (Heidelberg, Germany). All experiments were performed between passage 2 and 6.

Assessment of the Transfer of MPs to Endothelial Cells

In order to test the hypothesis of a transfer of MPs to endothelial cells, HUVECs were incubated with fluorescent circulating MPs from patients with cirrhosis. After 24 hours, the percentage of fluorescent HUVECs was analyzed on a LSR II flow cytometer (BD Biosciences, San Jose, Calif.) (see Supplementary Methods for details).

Western Blotting

Detection of COX-1, COX-2, NOS-2, NOS-3 and prostacyclin synthase on rat aortic rings and HUVECs incubated for 24 hours with MPs from patients with cirrhosis at their circulating concentration, supernatant or DMEM was performed by western blot analysis (see Supplementary Methods for details).

In Vivo Blood Pressure Measurement

C57Bl/6 mice weighting 27 to 33 g were injected retroorbitally with circulating MPs from patients with cirrhosis or the same volume of the corresponding 20500 g supernatant. Two hours later, blood arterial pressure was measured before and after phenylephrine injection (see Supplementary Methods for details).

Statistics

Quantitative variables were expressed as median (range) and categorical variables as absolute and relative frequencies. Comparisons between groups of independent quantitative variables were performed using Mann-Whitney test. Wilcoxon test was used for paired variables (e.g. effect of MPs and supernatant from the same patient). Comparisons between groups of qualitative variables were performed using chi-square test and the Fisher exact test, as appropriate. An analysis of variance (ANOVA) for repeated measures was used to evaluate the concentration-response curves to phenylephrine and acetylcholine. Spearman's correlation coefficient was used to test the correlation between circulating MP levels and clinical, laboratory and hemodynamic variables. Cumulative transplantation-free survival curves were calculated by Kaplan-Meier method. Patients who underwent liver transplantation were counted as censored. The potential relation of circulating MP level with the risk of death was analyzed by Cox regression univariate analysis. All tests were two-sided and used a significance level of 0.05. Data handling and analysis were performed with SPSS 12.0 (SPSS Inc., Chicago, Ill.).

Results:

Cellular Origin of MPs from Patients with Cirrhosis

Figure 1B:
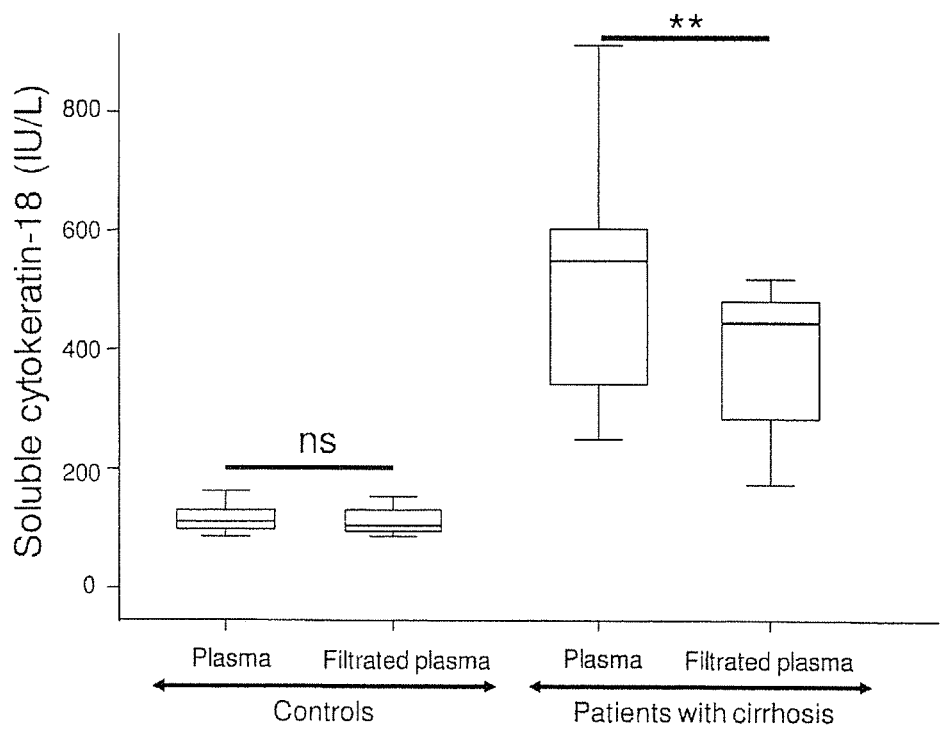

We first compared circulating MP levels and cellular origins in the 26 patients with cirrhosis from the pilot cohort and in 30 healthy controls. Age and prevalence of cardiovascular risk factors were not different between patients and controls except for a lower prevalence of dyslipidemia and a lower body mass index in the former group (Supplemental Table 1). Despite this lower prevalence of dyslipidemia and a lower body mass index (dyslipidemia and obesity being known to be associated with increased CD31+MPs)[10], circulating levels of leuko-endothelial (CD31+/41−), pan-leukocyte (CD11a+), lymphocyte (CD4+) and erythrocyte (CD235a+) MPs were higher in patients with cirrhosis than in controls (FIG. 1A). As circulating MPs harboring cytokeratin-18, a hepatocyte marker, could not be detected using flow cytometry analysis, ELISA assays were conducted. As shown in FIG. 1B, plasma from patients with cirrhosis contained hepatocyte-derived MPs whereas plasma from controls did not. No differences were observed in circulating annexin V+ MP and MPs from other cellular origin.

In order to identify the factors responsible for the increase in circulating CD31+/41−, CD11a+, CD4+, CD235a+ and cytokeratin-18+MP levels in patients with cirrhosis, we included 65 additional patients with cirrhosis. Their characteristics at inclusion were not different from those of the 26 patients from the pilot cohort. The features of all the 91 patients (i.e., the 26 patients from the pilot cohort and the 65 additional patients) are presented in Table 1. Out of these 91 patients, 31 underwent liver transplantation and 16 died. Cause of death was infection, alcoholic hepatitis, bleeding, encephalopathy and unknown in 9, 2, 2, 1 and 2 patients respectively. Median follow-up was 7.1 (0-46.5) months. Six- and 12-month survival rates were 84 and 77% respectively.

Figure 1C:
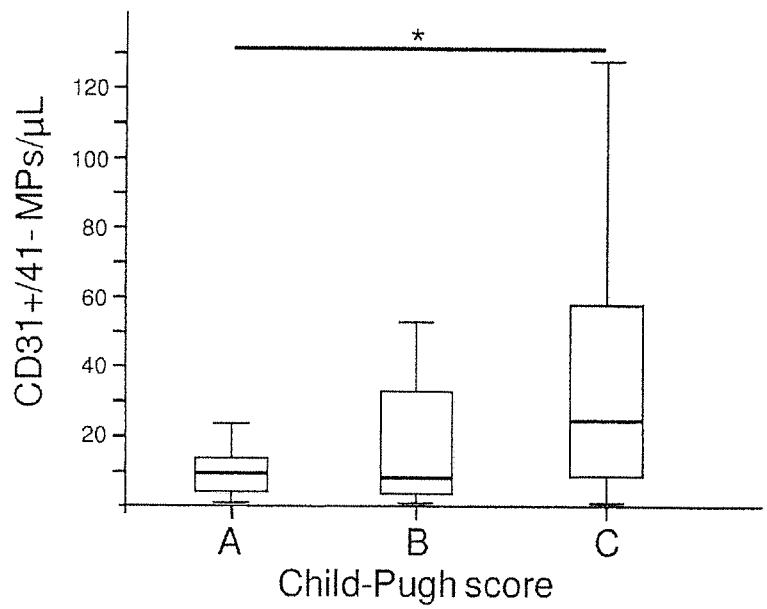
Figure 1D:
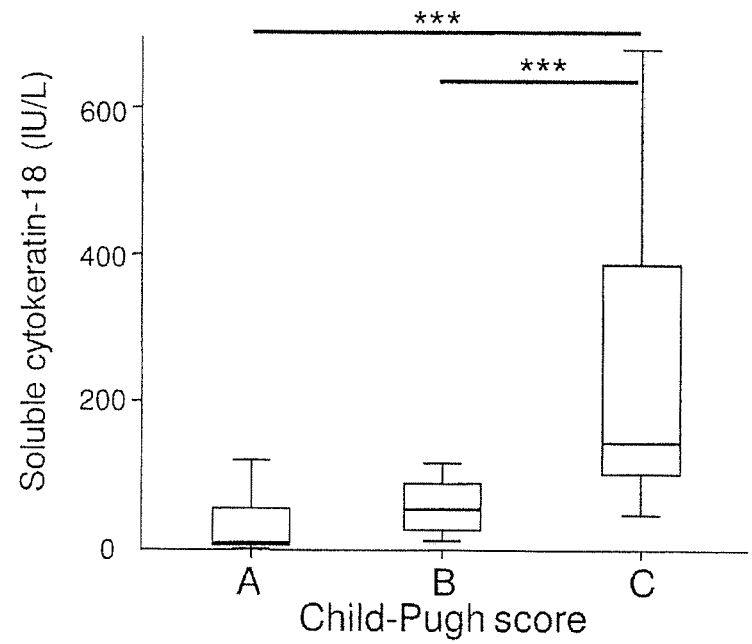

The circulating levels of MPs of leuko-endothelial (CD31+/41−) and hepatocyte origin (cytokeratin-18+) increased with cirrhosis severity, as attested by the strong correlations with MELD score, Child-Pugh score (FIGS. 1C and 1D), prothrombin index, serum bilirubin level, and the inverse correlation with serum albumin level (Table 2). Moreover, patients with hepatic encephalopathy had 3.5 fold more MPs of leuko-endothelial origin than those without [39 (6-438) vs. 11 (0-259) CD31+/41− MPs/µL; n=18 vs. 71; p=0.007] and patients with ascites had 4 fold more MPs of hepatocyte origin than those without [126 (10-680) vs. 31 (0-147) IU/L soluble cytokeratin-18 bound to MPs; n=30 vs. 10; p=0.008). Moreover, CD31+/41− MP levels were significantly associated with survival (risk ratio: 2.044; 95% confidence interval: 1.290-3.239; 16 events; p=0.002; for $10^2$×CD31+/41− MPs/µL).

The circulating levels of MPs of leuko-endothelial origin and of hepatocyte origin also correlated with markers of systemic inflammation, i.e. C-reactive protein and leukocyte count and with markers of hepatocyte damage such as AST level (Table 2).

MPs of leuko-endothelial origin or of hepatocyte origin did not correlate with any hemodynamic parameter, likely because these parameters were not available for all stages of the disease, and only for the most seriously ill patients: 2 out of the 47 patients with available hepatic venous pressure gradient measurement and none of the 24 patients with right heart catheterization were Child-Pugh A. Indeed, such hemodynamic measurements were performed at the time of transjugular liver biopsy, a route restricted in our centre to patients with haemostatic defects and/or ascites, as recommended earlier[11].

There was no influence of age, body mass index, hypertension, smoking, diabetes, cause of cirrhosis, beta-blockers use, diuretics intake, platelet count, on circulating CD31+/CD41−, CD11a+, CD4+, CD235a+ and cytokeratin-18+ MPs levels in the 91 patients with cirrhosis. Antibiotics intake and female gender were only weakly associated with an increase in hepatocyte MPs [142 (83-680) vs. 83 (0-587) IU/L soluble cytokeratin-18+ bound to MPs; n=9 vs. 30; p=0.028] and in pan-leukocyte MPs levels [55 (0-2484) vs. 35 (2-1445) CD11a+MP/4; n=23 vs. 65; p=0.047) respectively, and dyslipidemia with a decrease in erythrocyte MP level [32 (10-50) vs. 73 (2-1814) CD235a+ MP/μL; n=6 vs. 83; p=0.01].

MPs from Patients with Cirrhosis Impair Response to Vasoconstrictive Agents

Figure 2A:
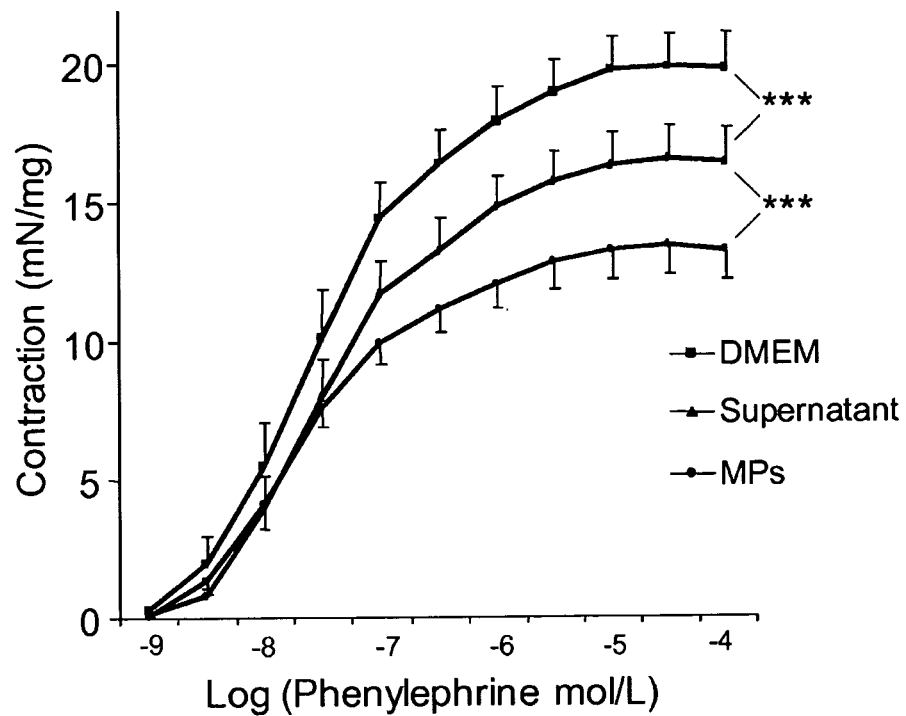
FIG. 2. Circulating MPs from patients with decompensated cirrhosis induce arterial hyporeactivity to vasoconstrictors. A-C. Concentration-response curves to phenylephrine of healthy rats aortic rings previously incubated for 24 hours with plasma MPs at their circulating concentration, or with controls i.e. plasma supernatant or DMEM. MPs from patients with Child-Pugh B or C cirrhosis impair contraction to phenylephrine (n=9) (A), while MPs from healthy controls (n=4) (B) or MPs from Child-Pugh A patients (n=7) (C) have no effect.
Figure 2B:
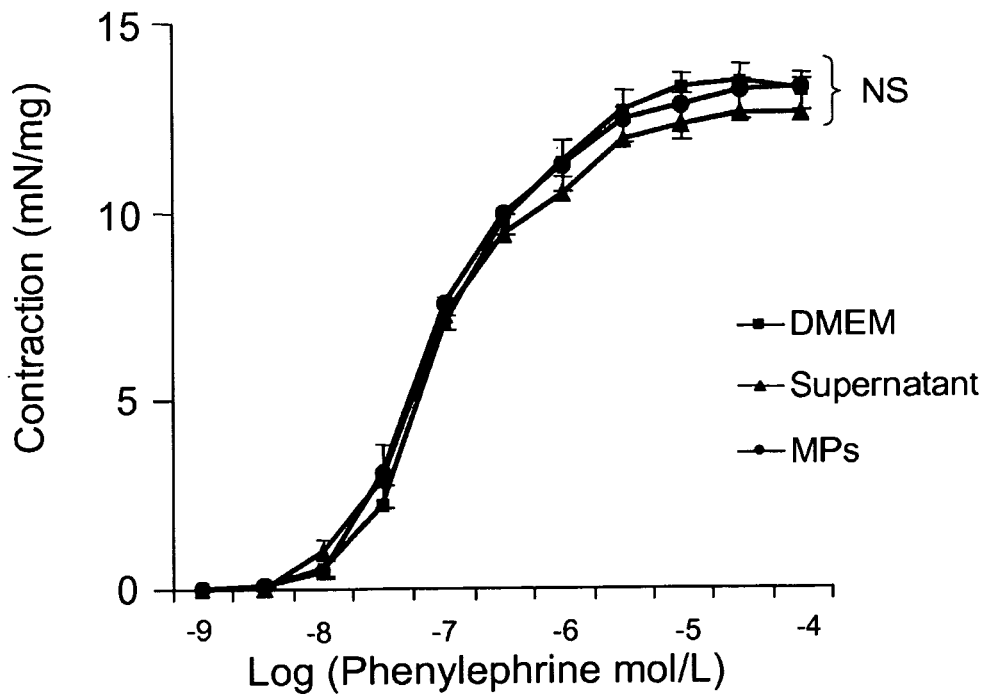
Figure 2C:
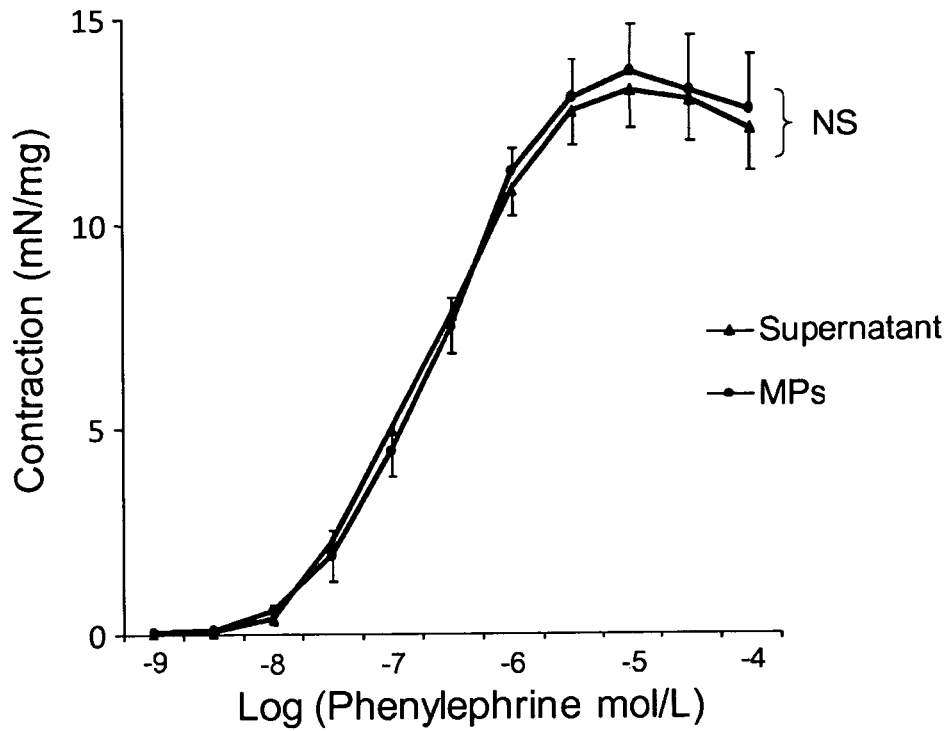

As systemic vasodilation plays a major role in the pathogenesis of the complications of chronic liver diseases[12], and as MPs modulate vascular reactivity in several vascular pathologies[2], we then assessed the potential role of MPs from patients with cirrhosis on systemic vasodilation using conventional organ chamber assays. Exposure of rat aortic rings for 24 hours to plasma MPs from patients with decompensated cirrhosis (Child-Pugh B or C) at their circulating concentration impaired response to phenylephrine while MPs from patients with compensated cirrhosis (Child-Pugh A) or from healthy controls had no effect (FIG. 2 A to C). MPs' effect was not dependent upon the cause of the liver disease, since it was induced with MPs from patients with alcoholic as well as hepatitis C virus related cirrhosis (data not shown). MPs' effect was also observed with healthy human mesenteric arteries, as well as with aortas from rats with cirrhosis. Unless otherwise stated, the following experiments were performed using circulating MPs from Child-Pugh B or C patients incubated for 24 hours with aortic rings from healthy rats. Neither MPs from patients with cirrhosis nor from healthy controls modified endothelium-dependent relaxation to acetylcholine.

Figure 3A:
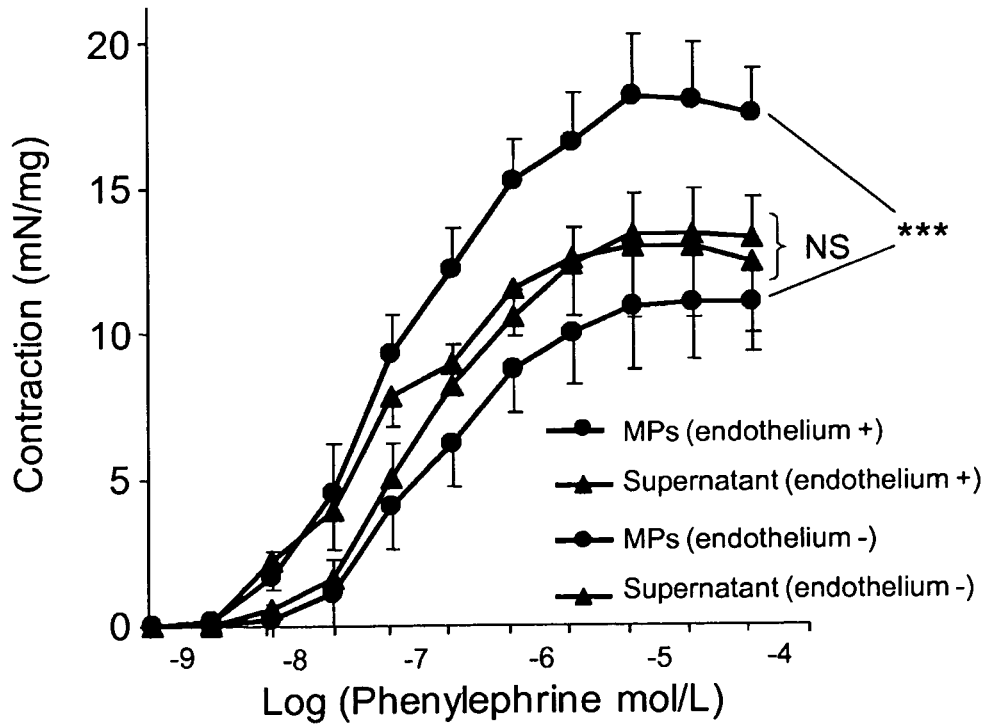
FIG. 3. Arterial hyporeactivity to vasoconstrictors induced by circulating MPs from patients with cirrhosis is endothelium- and cyclo-oxygenase (COX)-1 dependant. A to E. Healthy rat aortic rings were incubated for 24 hours with plasma MPs from patients with Child-Pugh B or C cirrhosis at their circulating concentration, or with supernatant. A. Gently mechanically removing endothelium restores contraction to phenylephrine of aortic rings incubated with MPs but had no effect on rings exposed to supernatant (n=4). B. Exposure for 45 minutes of aortic rings to an inhibitor of NO-synthases (L-Nitro arginine, L-NA; $10^{-4}$ mol/L) did not restore contraction to phenylephrine (n=6). C. Exposure for 45 minutes of aortic rings to an inhibitor of COX (diclofenac; $10^{-6}$ mol/L) suppressed MPs effect (n=6). D. Exposure for 45 minutes of aortic rings to an inhibitor of COX-1 (SC-560; $10^{-6}$ mol/L) improved response to phenylephrine while an inhibitor of COX-2 (NS-398; $10^{-6}$ mol/L) had no effect (n=5). E. COX-1 level, assessed using western blot, was not increased in aortic rings incubated for 24 hours with circulating MPs from patients with cirrhosis at their circulating concentration as compared to control conditions (DMEM or supernatant) (n=6). Data are mean±SEM. NS, no significant difference; , p<0.01; *, p<0.001.
Figure 3B:
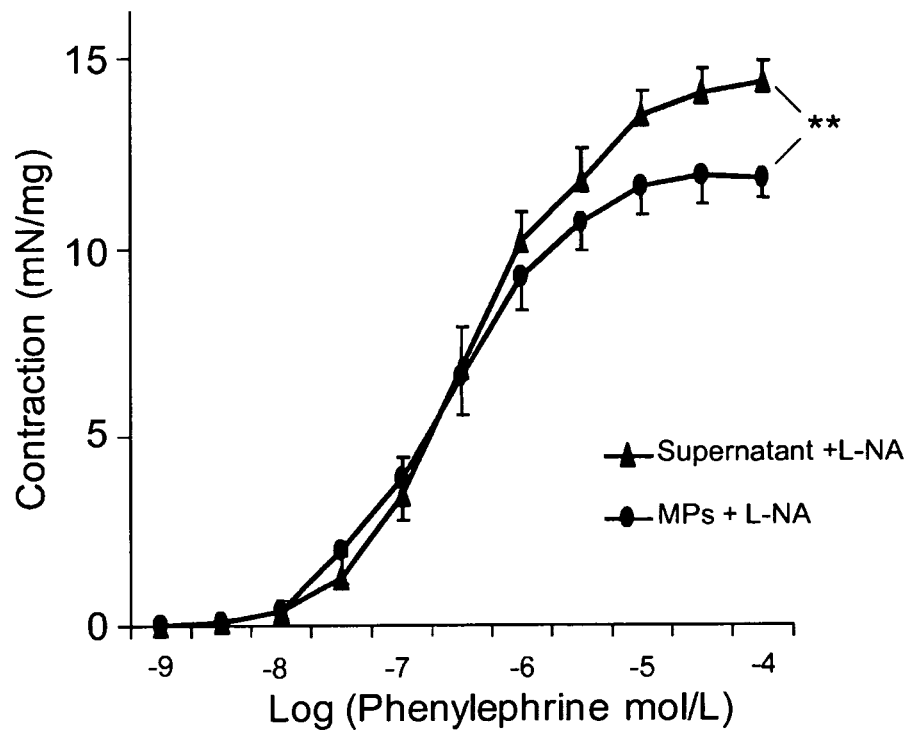
Figure 3C:
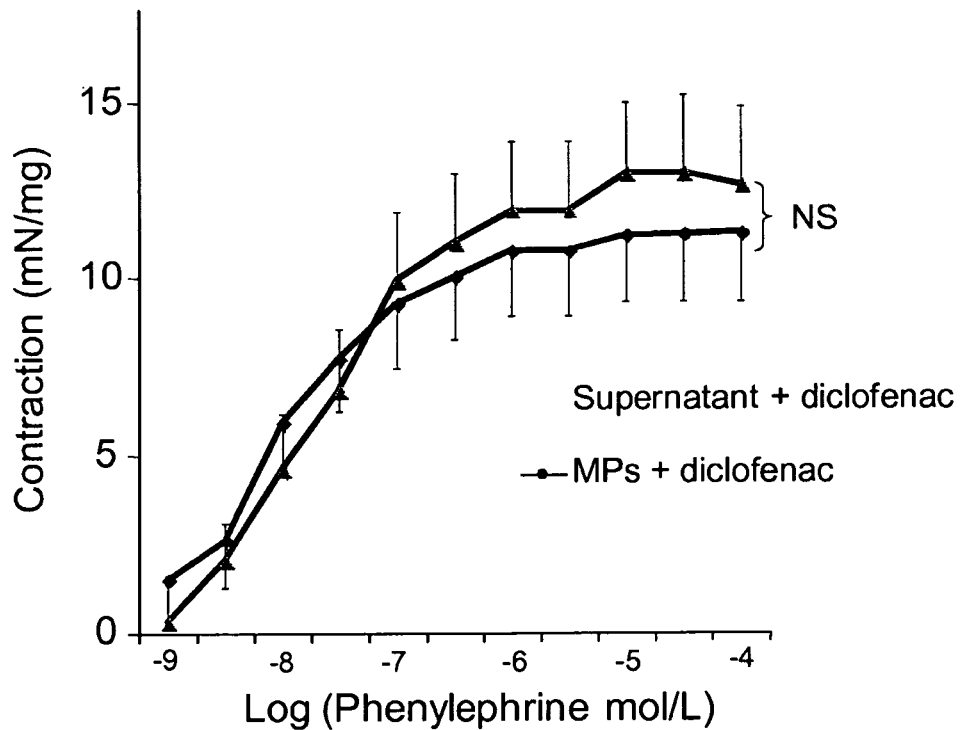
Figure 3D:
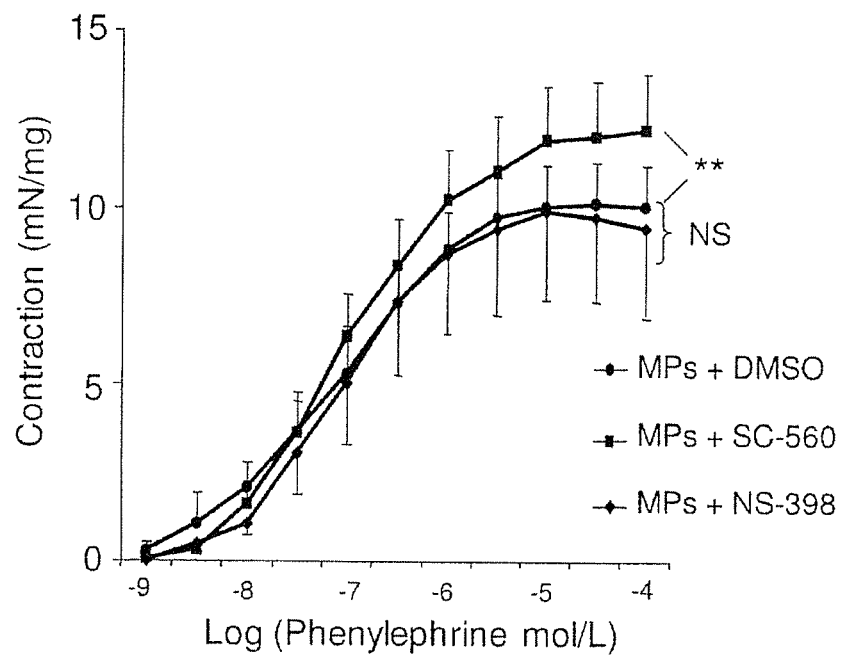
Figure 3E:
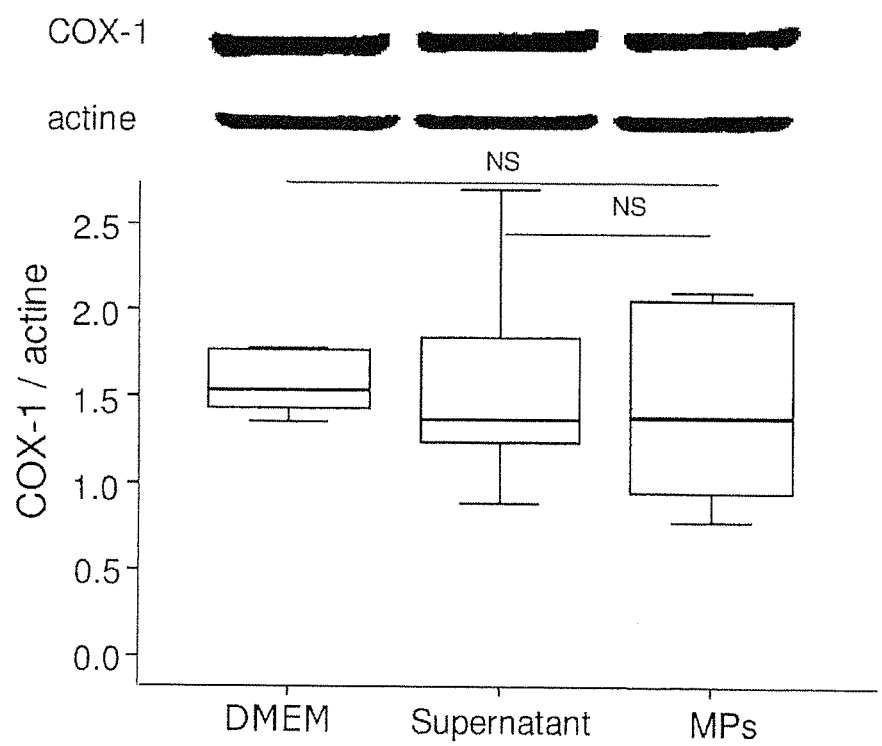

MPs from Patients with Cirrhosis Impair Response to Phenylephrine in a COX-1 Dependant Manner We then sought to evaluate the molecular mechanisms leading to the impaired response to vasoconstrictive agents following exposure to circulating MPs from patients with cirrhosis. As shown in FIG. 3A, mechanically removing endothelium from aortic rings restored contraction to phenylephrine, demonstrating that MP treatment induced vascular hyporeactivity results from the release of vasodilatory factors from endothelial cells. To investigate the potential role of nitric oxide and COX metabolites, the effect on response to phenylephrine of a nitric oxide-synthase inhibitor (L-Nitro arginine), of a non-selective COX inhibitor (diclofenac) and of selective inhibitors of COX-1 (SC-560) and of COX-2 (NS-398) were examined. Contractions to phenylephrine were significantly increased following exposure to diclofenac and SC-560, whereas L-Nitro arginine and NS-398 had no effect, suggesting a COX-1-dependent and NO-synthase-independent mechanism (FIG. 3B to 3D). In accordance with these results, the end-metabolite of the vasodilator prostacyclin, 6-keto PGF1a, was increased following exposure of aortic rings to MPs [210 (207-1137) vs. 136 (65-238) pg/mL in the medium of aortic rings incubated with MPs and supernatant, respectively; n=3]. MPs from patients with cirrhosis at their circulating concentration did not change the expression of COX-2, NO-synthase 2, and NO-synthase 3 protein levels, in rat aortic rings and in HUVECs (western blot analysis; 24 hours; n=6 to 8; data not shown). MPs from patients with cirrhosis did also not modify COX-1 level in aortic rings (FIG. 3E) or HUVECs (COX-1/actine: MPs: 1.06±0.19 vs. supernatant 1.05±0.12; p=0.866; n=7; 24 hours). Prostacyclin synthase protein levels in rat aortic rings or in HUVECs were also not different between MP and supernatant treated aortic rings or HUVECs (western blot analysis; 24 hours; n=8). To confirm this lack of implication of protein synthesis, response to phenylephrine was assessed after incubation of aortic rings with actinomycin D (2 μg/mL). This inhibitor of transcription did not modify MPs' effect on the response to phenylephrine: response to phenylephrine $10^{-4}$ mol/L was 11.1 (8.9-11.8) mN/mg for aortic rings incubated with MPs vs. 13.8 (11.3-16.2) mN/mg with supernatant (p=0.046; n=6).

Figure 4A:
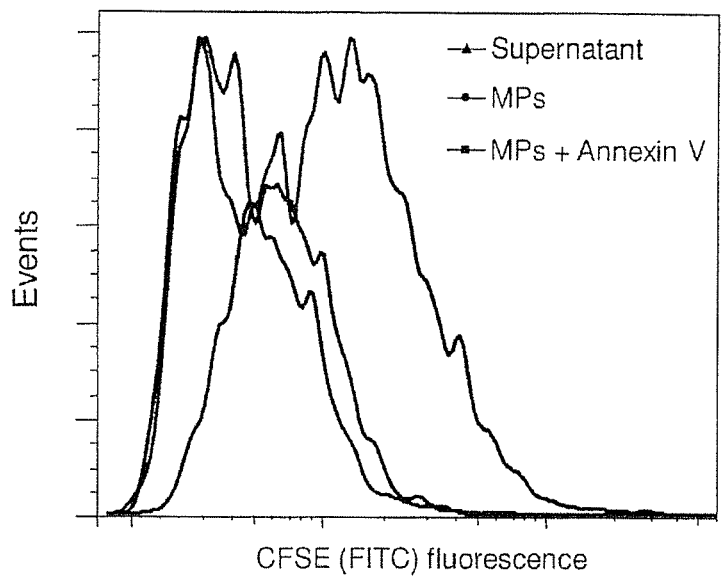
FIG. 4. Cirrhotic MP effect depends upon a transfer of MPs to endothelial cells. A and B. Circulating MPs from cirrhotic patients were labelled with the fluorescent dye CFSE, washed to remove unbound dye, incubated for 30 minutes with $CaCl_2$ (5 mmol/L final concentration) with or without annexin V (4 µg/mL), and then exposed, at their circulating concentration, for 24 hours to HUVECs. As compared to HUVECs exposed to the washing supernatant (green line), those incubated with fluorescent MPs became fluorescent (red line). Preincubation with annexin V decreased the up-take of fluorescent MPs by HUVECs (blue line). A. Representative flow cytometry fluorescence histogram. B. Data are median (horizontal bar), 25th and 75th percentile (boxes), and extreme values which are less than 3 box lengths from either end of the box (error bar) and given as the difference in CFSE+ HUVECs per well between MPs exposed cells and control conditions (supernatant with or without annexin V). C, D. Healthy rat aortic rings were incubated for 24 hours with plasma MPs from patients with Child-Pugh B or C cirrhosis at their circulating concentration, or with supernatant. Then, response to phenylephrine was assessed. Pre-incubation for 30 minutes with annexin V either with annexin V (4 µg/mL) in the presence of CaCl2 (5 mmol/L) suppressed cirrhotic MP effect (C, n=6). Data are mean±SEM. NS, no significant difference; *p<0.05; p<0.01; *p<0.001.
Figure 4B:
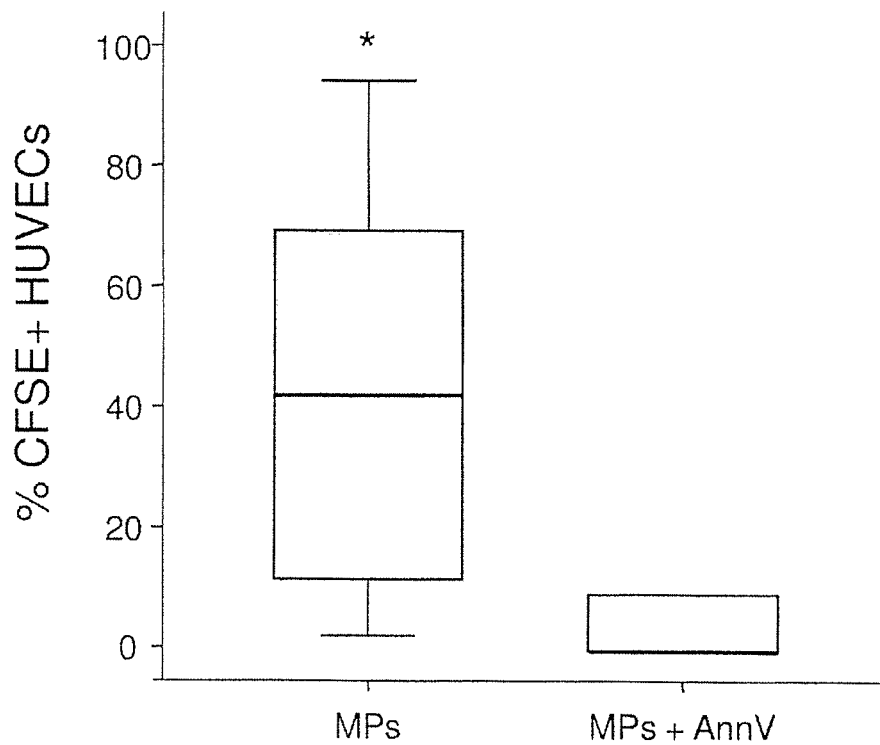
Figure 4C:
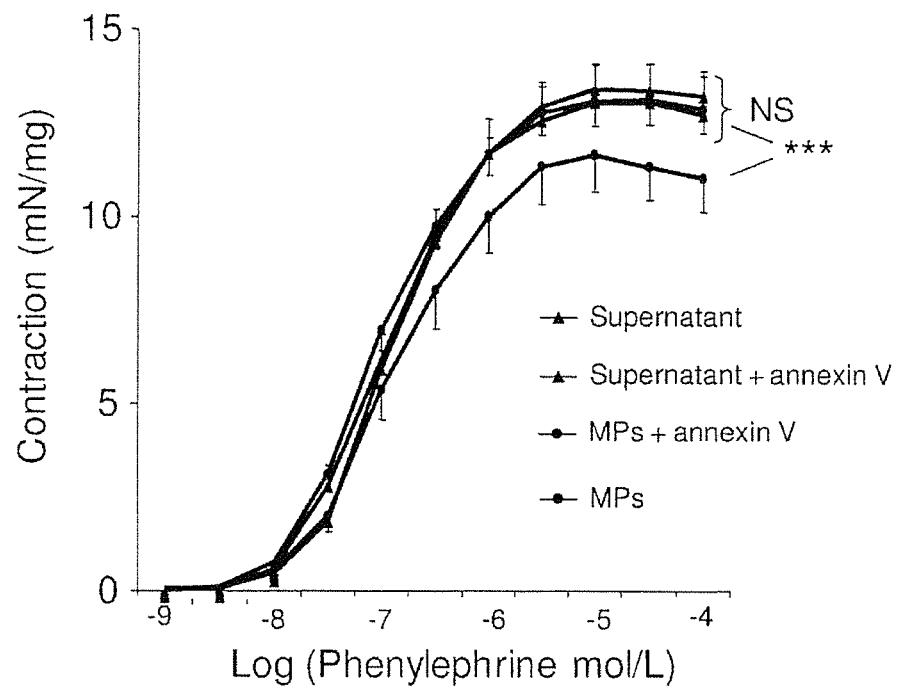

MPs from Patients with Cirrhosis Impair Response to Phenylephrine by Transferring Substrate for the Arachidonic Acid Metabolism Pathway Given the absence of increase in COX-1 protein level and the lack of effect of protein synthesis inhibitor, we hypothesized that MPs from patients with cirrhosis transfer substrate for the arachidonic acid metabolism pathway to endothelial cells. The first hint came from experiments showing that arachidonic acid ($10^{-5}$ mol/L for 2 hours) impaired the maximal response to phenylephrine, therefore mimicking the effect of cirrhotic MPs on vascular reactivity (n=4, p=0.009). To test this hypothesis, MPs were labelled with the fluorescent dye CFSE and incubated with HUVECs. After 24 hours, 44 (4-97) % of HUVECs exposed to MPs were CFSE+ as compared to only 2 (0-4) % of those incubated with supernatant (p=0.028; n=6) (FIG. 4A). As anionic phospholipids, such as phosphatidylserine, have been implicated in such an uptake of MPs by endothelial cells[5, 13], we then examined the effect of annexin V that binds to phosphatidylserine. Preincubation of MPs with annexin V (in the presence of 5 mmol/L $CaCl_2$) decreased endothelial fluorescence resulting from cirrhotic MP exposure by 100% (34-100) (FIGS. 4A and B) and restored the maximal contractile response to phenylphrine (FIG. 4C). Similar findings were obtained using diannexin, an annexin V homodimer[14]. Quinacrine, an inhibitor of phospholipase A2, also suppressed effect of cirrhotic MPs on the contractile response to phenylephrine: after quinacrine dihydrochloride ($3.10^{-5}$ mol/L) preincubation, response to phenylephrine $10^{-4}$ mol/L was 12.1 (10.5-14.8) mN/mg for aortic rings incubated with MPs vs. 12.7 (4.6-19) mN/mg with supernatant (p=0.767; n=9). Taken altogether, these results suggest that MPs membrane phospholipids are transferred to endothelial cells and act as substrate for phospholipase A2 production of arachidonic acid metabolites.

MPs from Patients with Cirrhosis Decrease Arterial Blood Pressure In Vivo

Figure 5:
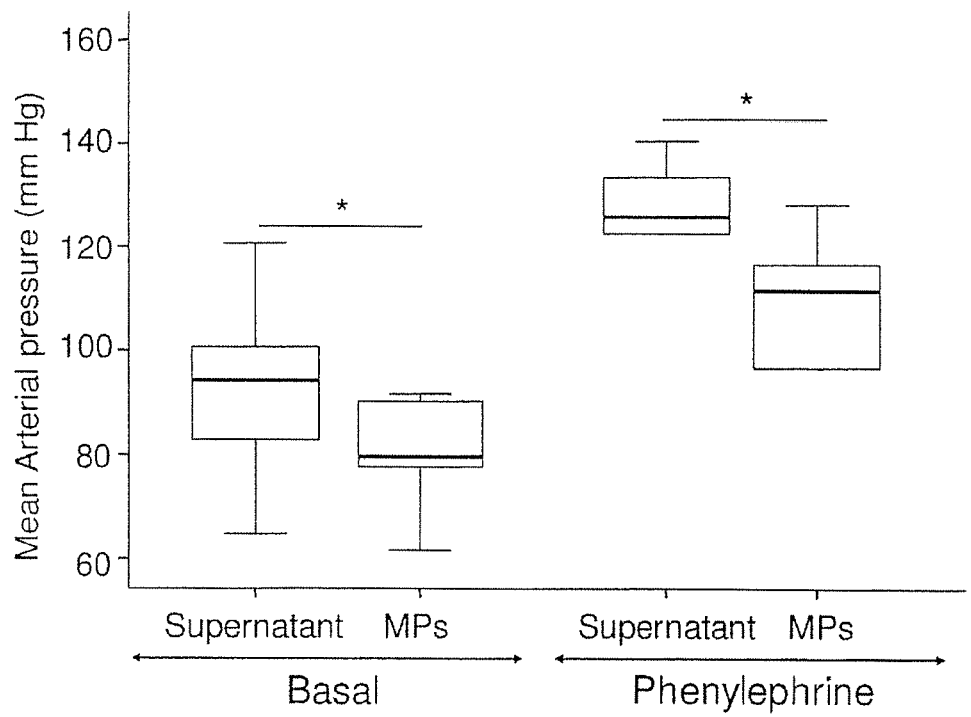
FIG. 5. MPs from patients with cirrhosis induce arterial hypotension in vivo. Mice were injected intravenously with MPs from patients with cirrhosis (to reach in mice blood a concentration in cirrhotic MPs corresponding to 60% of the circulating concentration in patient) or the corresponding supernatant. Two hours later, mice were anaesthetized and tail blood arterial pressure was measured spontaneously and after injection of phenylephrine 20 µg/kg body weight injected intravenously. As compared to mice receiving supernatant, mice receiving MPs had a lower mean arterial pressure both spontaneously (n=6) and after phenylephrine injection (n=5). Data are given as median (horizontal bar), 25th and 75th percentile (boxes), and extreme values which are less than 3 box lengths from either end of the box (error bar). *p<0.05.

We next assessed the in vivo relevance of these findings. Given the rapid clearance of MPs in vivo, a time point of 2 hours was chosen[15-16]. As shown in FIG. 5, intravenous injection of MPs from patients with cirrhosis decreased blood pressure in mice both under basal conditions and following phenylepherine injection.

Discussion:

The present study demonstrates that the plasma of patients with cirrhosis contain high levels of MPs of leuko-endothelial, of lymphocyte and of hepatocyte origin. Circulating MPs from patients with advanced cirrhosis contribute to systemic vasodilation of cirrhosis. Indeed, they are taken up by endothelial cells and induce arterial hyporeactivity to vasoconstrictor agents in a phosphatidylserine- and COX-1 dependent manner.

We observed here that levels of circulating MPs derived from leukocytes, endothelial cells, and hepatocytes were greater in patients with cirrhosis than in healthy controls. Interestingly, plasma levels of these specific MP subtypes augment with cirrhosis severity. This increase likely results from an overproduction of MPs. MPs are known to be released following cell activation or apoptosis[17], and hepatocyte apoptosis occurs in chronic liver diseases such as viral hepatitis C and alcoholic hepatitis[18]. Monocytes from patients with cirrhosis are activated in basal conditions[19]. Moreover, the plasma of patients with cirrhosis contains endotoxin, a stimulus known to induce MP release from monocytes and macrophages[20-21]. The increase in proinflammatory cytokines in the plasma of patients with cirrhosis could induce the release of MPs by endothelial cells[22-23]. The hypothesis of a role of systemic inflammation in the formation of MPs in cirrhosis is reinforced by the correlation observed here between C-reactive protein on the one hand and MPs of leuko-endothelial and of hepatocyte origin levels on the other hand. An impaired MP clearance may also occur in cirrhosis, since the liver, with other organs, contributes to MPs clearance[16 15].

No influence of cardiovascular risk factors (i.e. age, body mass index, hypertension, smoking, diabetes, dyslipidemia, serum creatinin) on circulating MP level was observed in patients with cirrhosis, contrary what happens in patients without liver disease[2]. This suggests that the effect of cirrhosis on MP levels may mask other factors.

This study also shows for the first time that a proportion of the so-called "soluble cytokeratin-18", a promising tool for differentiating bland steatosis from steatohepatitis in nonalcoholic patients, is in fact carried by MPs[24]. Interestingly, this MP-bound cytokeratin-18 correlates with liver disease severity and systemic inflammation much better than the total "soluble cytokeratin-18" does (Table 2). This suggests that MP-bound cytokeratin-18 could be a useful marker of cirrhosis severity.

As MPs are not only markers of cell damage, but have also been proven as crucial effectors in several important biological functions, including vascular reactivity, we then assessed the potential contribution of MPs to systemic vasodilation. We observed that circulating MPs from patients with advanced cirrhosis impair ex vivo arterial contraction to phenylephrine, whereas MPs from Child-Pugh A cirrhotic patients or healthy controls did not. This effect was obtained not only on aortic rings from healthy but also from cirrhotic rats, as well as on human mesentery artery. The significant decrease in arterial blood pressure observed in mice injected with cirrhotic MPs strongly suggests that these MPs induce vascular hypocontractility in vivo, and indicate that circulating MPs might contribute to systemic vasodilation occurring in liver diseases[12].

Our study demonstrates that the effect of MPs from patients with advanced cirrhosis depends on their uptake by endothelial cells in a phosphatidylserine-, phospholipase A2- and COX1-dependent manner, without COX1 protein overexpression. MPs deliver membrane phospholipids to endothelial cells, which are subsequently metabolized by several enzymes including phospholipase A2 and COX-1, leading to the formation of vasodilatory prostaglandins, and hyporeactivity to vasoconstrictors. The cell origin of the MPs responsible for this effect is so far unknown. As there is no difference in Annexin+ MPs levels between patients with cirrhosis and controls, other characteristics of MPs besides their exposure of phosphatidylserine should be involved.

This deleterious effect of MPs on systemic vasodilation through the COX-1 pathway is reminiscent of the studies on intrahepatic resistance by the group of Bosch and Garcia-Pagan. These authors have shown that COX-1-derived prostanoids induce intrahepatic vasoconstriction, favoring the increase in resistance to portal blood flow in cirrhotic livers[25]. Two hypotheses could explain these differences, i.e. a COX-1 dependent intrahepatic vasoconstriction and a systemic hyporesponsiveness to vasoconstrictors. First, circulating MPs may not have the same concentration and lipid composition in portal vein and in systemic circulation. Indeed, the liver is a major determinant of MP clearance[16]. Second, the phenotypic heterogeneity of sinusoidal and systemic endothelial cells is likely to affect the metabolism of arachidonic acid[26].

In conclusion, cirrhosis is associated with an increase in several circulating MP subpopulations, likely resulting from systemic inflammation and liver cell damage. Our results demonstrate that MPs circulating in the blood of patients with advanced cirrhosis induce arterial hypocontractility and thus must contribute systemic vasodilation.

TABLE 1

Baseline characteristics of the 91 patients with cirrhosis.

| Characteristics | |
|---|---|
| Age (yrs) | 56 (36-82) |
| Male gender - N (%) | 68 (75) |
| Cause of cirrhosis - N (%) | Alcohol: 71 (78) |
| | Hepatitis C: 20 (22) |
| Body mass index (kg · m$^{-2}$) | 24.1 (18.0-38.9) |
| Ascites - N (%) | 22 (24) |
| Encephalopathy - N (%) | 18 (20) |
| Esophageal varices (available in 77) - N (%) | 59 (77) |
| Child-Pugh score (A, B, C) | 16 (18), 18 (20), 57 (62) |
| Model for end-stage liver disease (MELD) score | 14.4 (0-44.0) |
| Cardio-vascular risks factors | |
| Hypertension - N (%) | 18 (20) |
| Smoking - N (%) | 44 (48) |
| Diabetes - N (%) | 20 (22) |
| Dyslipidemia - N (%) | 6 (7) |
| Treatments | |
| Beta-blockers - N (%) | 36 (40) |
| Diuretics- N (%) | 37 (41) |
| Antibiotics - N (%) | 23 (26) |
| Serum levels | |
| Leukocytes (×10$^9$/L) | 6.0 (1.1-22.5) |
| Hemoglobin (g/L) | 111 (69-165) |
| Platelet count (×10$^9$/L) | 106 (28-356) |
| Prothrombin index (%) | 43 (9-103) |
| Creatinine (μmol/L) | 65 (39-150) |
| Albumin (g/L) | 26 (9-53) |
| Aspartate aminotransferase (× upper limit of normal) | 2.4 (0.9-7.3) |

TABLE 1-continued

Baseline characteristics of the 91 patients with cirrhosis.

| | |
|---|---|
| Alanine aminotransferase (x upper limit of normal) | 1.0 (0.3-6.4) |
| Bilirubin (μmol/L) | 58 (6-798) |
| C reactive protein (available in 75) (mg/L) | 13 (0-115) |
| Hemodynamic Data | |
| Hepatic venous pressure gradient (mm Hg) (available in 47) | 18 (7-36) |
| Central venous pressure (mm Hg) (available in 47) | 5 (0-17) |
| Mean pulmonary artery pressure (mm Hg) (available in 24) | 16 (8-30) |
| Pulmonary capillary wedge pressure (mm Hg) (available in 24) | 10 (0-26) |
| Cardiac index (L · min$^{-1}$ · m$^{-2}$) (available in 24) | 3.76 (2.28-7.10) |
| Systemic vascular resistances (dynes · s · cm$^{-5}$) (available in 24) | 800 (419-1667) |
| Mean arterial pressure (mm Hg) | 86 (63-113) |
| Circulating MP levels | |
| CD31+41− (MPs/μL) | 16 (0-438) |
| CD11a+ (MPs/μL) | 41 (0-2484) |
| CD4+ (MPs/μL) | 1 (0-83) |
| CD235a+ (MPs/μL) | 69 (2-1814) |
| Soluble cytokeratin-18 in native plasma (available in 40) | 480 (141-4603) |
| Soluble cytokeratin-18 in filtrated plasma (available in 40) | 402 (136-3951) |

Data are expressed as median (range) or frequency (%). Unless otherwise stated, data were available for all 91 patients.

In patients with hemodynamic assessment, liver and/or right heart catheterization, via a Swan-Ganz catheter, were performed within 48 hours of blood sample collection.

The upper limit of normal for aspartate aminotransferase was 31 UI/L in women and 35 UI/L in men. The upper limit of normal for alanine aminotransferase was 34 IU/L in women and 45 IU/L in men.

TABLE 2

Correlations between circulating MP levels and clinical, laboratory or hemodynamic parameters.

| | CD31+/41− MPs | CD11a+ MPs | CD4+ MPs | CD235a+ MPs | CK-18 in native plasma | CK-18 in filtrated plasma | MP bound CK-18 |
|---|---|---|---|---|---|---|---|
| Child-Pugh score | r = 0.29 P = 0.01 | r = 0.12 P = 0.27 | r = 0.16 P = 0.14 | r = 0.21 P = 0.05 | r = 0.32 P = 0.04 | r = 0.20 P = 0.22 | r = 0.65 P < 0.001 |
| MELD score | r = 0.34 P = 0.001 | r = 0.16 P = 0.15 | r = 0.16 P = 0.14 | r = 0.13 P = 0.24 | r = 0.37 P = 0.02 | r = 0.30 P = 0.06 | r = 0.58 P < 0.001 |
| Prothrombin index (%) | r = −0.26 P = 0.01 | r = −0.14 P = 0.20 | r = −0.10 P = 0.34 | r = −0.19 P = 0.07 | r = −0.31 P = 0.05 | r = −0.19 P = 0.23 | r = −0.64 P < 0.001 |
| Serum creatinine (μmol/L) | r = −0.08 P = 0.46 | r = −0.20 P = 0.06 | r = 0.00 P = 0.96 | r = −0.18 P = 0.10 | r = −0.23 P = 0.15 | r = −0.13 P = 0.43 | r = −0.38 P = 0.01 |
| Serum Albumin (g/L) | r = −0.24 P = 0.02 | r = −0.11 P = 0.30 | r = −0.15 P = 0.16 | r = −0.17 P = 0.11 | r = −0.16 P = 0.34 | r = −0.05 P = 0.77 | r = −0.49 P = 0.002 |
| Serum AST (x ULN) | r = 0.29 P = 0.01 | r = 0.26 P = 0.02 | r = 0.28 P = 0.01 | r = 0.17 P = 0.10 | r = 0.66 P < 0.001 | r = 0.60 P < 0.001 | r = 0.48 P = 0.002 |
| Serum ALT (x ULN) | r = 0.05 P = 0.62 | r = 0.02 P = 0.86 | r = 0.25 P = 0.02 | r = 0.11 P = 0.32 | r = 0.34 P = 0.03 | r = 0.34 P = 0.03 | r = 0.05 P = 0.76 |
| Serum bilirubin (μmol/L) | r = 0.45 P < 0.001 | r = 0.23 P = 0.04 | r = 0.23 P = 0.03 | r = 0.21 P = 0.05 | r = 0.48 P = 0.002 | r = 0.39 P = 0.01 | r = 0.69 P < 0.001 |
| Leukocytes (×10$^9$/L) | r = 0.34 P = 0.001 | r = 0.11 P = 0.29 | r = 0.21 P = 0.05 | r = 0.09 P = 0.41 | r = 0.38 P = 0.02 | r = 0.33 P = 0.04 | r = 0.37 P = 0.02 |
| Hemoglobin (g/L) | r = −0.21 P = 0.05 | r = −0.15 P = 0.17 | r = −0.03 P = 0.75 | r = −0.09 P = 0.43 | r = −0.25 P = 0.11 | r = −0.18 P = 0.26 | r = −0.52 P < 0.001 |
| Platelet count (×10$^9$/L) | r = 0.03 P = 0.76 | r = 0.05 P = 0.65 | r = −0.01 P = 0.96 | r = −0.15 P = 0.16 | r = −0.17 P = 0.30 | r = −0.10 P = 0.56 | r = −0.26 P = 0.11 |
| C Reactive Protein (mg/L) | r = 0.38 P = 0.001 | r = 0.00 P = 0.97 | r = 0.23 P = 0.05 | r = 0.11 P = 0.37 | r = 0.34 P = 0.05 | r = 0.25 P = 0.15 | r = 0.53 P = 0.001 |
| Cardiac index (L · min$^{-1}$ · m$^{-2}$) | r = −0.25 P = 0.25 | r = −0.13 P = 0.545 | r = −0.08 P = 0.702 | r = −0.11 P = 0.61 | r = 0.16 P = 0.546 | r = 0.10 P = 0.720 | r = 0.25 P = 0.35 |
| Systemic vascular resistances (dynes · s · cm$^{-5}$) | r = 0.28 P = 0.19 | r = 0.08 P = 0.73 | r = 0.08 P = 0.720 | r = 0.08 P = 0.73 | r = −0.12 P = 0.66 | r = −0.07 P = 0.79 | r = −0.19 P = 0.48 | r, Spearman correlation coefficient.
Correlations with hemodynamic parameters were tested in 24 patients for CD11a+, CD31+/41− and CD4+ MPs and in 14 patients for soluble cytokeratine-18. Other correlations were assessed in 91 patients for CD11a+, CD31+/41− and CD4+ MPs and in 40 patients for soluble cytokeratine-18.
Abbreviations: AST, Aspartate aminotransferase; ALT, Alanine aminotransferase; CK-18, soluble cytokeratin-18; MELD, model for end-stage liver disease; MPs, microparticles; ULN, upper limit of normal.
Bold text indicates significant correlations between MP levels and clinical, laboratory or hemodynamic parameters.

REFERENCES

Throughout this application, various references describe the state of the art to which this invention pertains. The disclosures of these references are hereby incorporated by reference into the present disclosure.

1. Hennenberg M, Trebicka J, Sauerbruch T, Heller J. Mechanisms of extrahepatic vasodilation in portal hypertension. *Gut*. September 2008; 57(9):1300-1314.
2. Amabile N, Rautou P E, Tedgui A, Boulanger C M. Microparticles: key protagonists in cardiovascular disorders. *Semin Thromb Hemost*. November 2010; 36(8):907-916.
3. Bernimoulin M, Waters E K, Foy M, et al. Differential stimulation of monocytic cells results in distinct populations of microparticles. *J Thromb Haemost*. June 2009; 7(6):1019-1028.
4. Huber J, Vales A, Mitulovic G, et al. Oxidized membrane vesicles and blebs from apoptotic cells contain biologically active oxidized phospholipids that induce monocyte-endothelial interactions. *Arterioscler Thromb Vasc Biol*. January 2002; 22(1):101-107.
5. Rautou P E, Leroyer A S, Ramkhelawon B, et al. Microparticles From Human Atherosclerotic Plaques Promote Endothelial. ICAM-1-Dependent Monocyte Adhesion and Transendothelial Migration. *Circ Res*. Dec. 16, 2011.
6. Mause S F, Weber C. Microparticles: protagonists of a novel communication network for intercellular information exchange. *Circ Res*. Oct. 29, 2010; 107(9):1047-1057.
7. Amabile N, Guerin A P, Leroyer A, et al. Circulating endothelial microparticles are associated with vascular dysfunction in patients with end-stage renal failure. *J Am Soc Nephrol*. November 2005; 16(11):3381-3388.
8. Boulanger C M, Scoazec A, Ebrahimian T, et al. Circulating microparticles from patients with myocardial infarction cause endothelial dysfunction. *Circulation*. Nov. 27, 2001; 104(22):2649-2652.
9. Lebrec D. Animal models in portal hypertension. *Portal Hypertension: Clinical and Physiological Aspects*. Tokyo, Japan: Springer-Verlag; 1991:101-113.
10. Pirro M, Schillaci G, Paltriccia R, et al. Increased ratio of CD31+/CD42− microparticles to endothelial progenitors as a novel marker of atherosclerosis in hypercholesterolemia. *Arterioscler Thromb Vasc Biol*. November 2006; 26(11):2530-2535.
11. Rockey D C, Caldwell S H, Goodman Z D, Nelson R C, Smith A D. Liver biopsy. *Hepatology*. March 2009; 49(3):1017-1044.
12. Blendis L, Wong F. The hyperdynamic circulation in cirrhosis: an overview. *Pharmacol Ther*. March 2001; 89(3):221-231.
13. Burger K N. Greasing membrane fusion and fission machineries. *Traffic*. August 2000; 1(8):605-613.
14. Teoh N C, Ito Y, Field J, et al. Diannexin, a novel annexin V homodimer, provides prolonged protection against hepatic ischemia-reperfusion injury in mice. *Gastroenterology*. August 2007; 133(2):632-646.
15. Dasgupta S K, Abdel-Monem H, Niravath P, et al. Lactadherin and clearance of platelet-derived microvesicles. *Blood*. Feb. 5, 2009; 113(6):1332-1339.
16. Willekens F L, Werre J M, Kruijt J K, et al. Liver Kupffer cells rapidly remove red blood cell-derived vesicles from the circulation by scavenger receptors. *Blood*. Mar. 1, 2005; 105(5):2141-2145.
17. Morel O, Jesel L, Freyssinet J M, Toti F. Cellular mechanisms underlying the formation of circulating microparticles. *Arterioscler Thromb Vasc Biol*. January 2011; 31(1):15-26.
18. Guicciardi M E, Gores G J. Apoptosis: a mechanism of acute and chronic liver injury. *Gut*. July 2005; 54(7):1024-1033.
19. Tazi K A, Quioc J J, Saada V, Bezeaud A, Lebrec D, Moreau R. Upregulation of TNF-alpha production signaling pathways in monocytes from patients with advanced cirrhosis: possible role of Akt and IRAK-M. *J Hepatol*. August 2006; 45(2):280-289.
20. Rasaratnam B, Kaye D, Jennings G, Dudley F, Chin-Dusting J. The effect of selective intestinal decontamination on the hyperdynamic circulatory state in cirrhosis. A randomized trial. *Ann Intern Med*. Aug. 5, 2003; 139(3):186-193.
21. Gauley J, Pisetsky D S. The release of microparticles by RAW 264.7 macrophage cells stimulated with TLR ligands. *J Leukoc Biol*. June 2010; 87(6):1115-1123.
22. Rautou P E, Vion A C, Amabile N, et al. Microparticles, vascular function, and atherothrombosis. *Circ Res*. Aug. 19, 2011; 109(5):593-606.
23. Thabut D, Tazi K A, Bonnefont-Rousselot D, et al. High-density lipoprotein administration attenuates liver proinflammatory response, restores liver endothelial nitric oxide synthase activity, and lowers portal pressure in cirrhotic rats. *Hepatology*. December 2007; 46(6):1893-1906.
24. Tamimi T I, Elgouhari H M, Alkhouri N, et al. An apoptosis panel for nonalcoholic steatohepatitis diagnosis. *J Hepatol*. June 2011; 54(6):1224-1229.
25. Bosch J, Abraldes J G, Fernandez M, Garcia-Pagan J C. Hepatic endothelial dysfunction and abnormal angiogenesis: new targets in the treatment of portal hypertension. *J Hepatol*. September 2010; 53(3):558-567.
26. Aird W C. Phenotypic heterogeneity of the endothelium: I. Structure, function, and mechanisms. *Circ Res*. Feb. 2, 2007; 100(2):158-173.

The invention claimed is:

1. A method for determining whether a patient with cirrhosis is at risk of having significant portal hypertension and preventing at least one complication therefrom including ascites, the method comprising:
   a) quantifying the levels of leuko-endothelial (CD31+/41−) microparticles, pan-leukocyte (CD11a+) microparticles, lymphocyte (CD4+) microparticles, erythrocyte (CD235a+) microparticles and hepatocyte-derived (cytokeratin-18+) microparticles in a blood sample obtained from the patient;
   b) comparing said levels at step a) with predetermined reference values obtained from subjects with no significant portal hypertension;
   c) determining an increase in the levels of each of the microparticles quantified at step a) as compared to the predetermined reference values at step b);
   wherein an increase in the levels of each of the microparticles quantified at step a) as compared to the predetermined reference values at step b) indicates that the patient is at risk of having significant portal hypertension and in need of preventive treatment; and,
   d) administering the patient with a preventive treatment for the at least one complication including ascites associated with significant portal hypertension or liver transplantation when the patient is determined as being at risk of having significant portal hypertension.

2. The method according to claim 1 wherein said preventive treatment is selected from the group consisting of administration of B-blockers and administration of vasoactive drugs.

3. The method according to claim 1, wherein said blood sample is a plasma sample.

4. The method according to claim 1, which comprises contacting the blood sample with a set of binding partners capable of selectively interacting with leuko-endothelial (CD31+/41−) microparticles, pan-leukocyte (CD11a+) microparticles, lymphocyte (CD4+) microparticles, erythrocyte (CD235a+) microparticles and hepatocyte-derived (cytokeratin-18+) microparticles present in the blood sample.

5. The method according to claim 4, wherein binding partners of said set of binding partners are polyclonal or monoclonal antibodies specifically directed against leuko-endothelial (CD31+/41−) microparticles, pan-leukocyte (CD11a+) microparticles, lymphocyte (CD4+) microparticles, erythrocyte (CD235a+) microparticles or hepatocyte-derived (cytokeratin-18+) microparticles.

6. The method according to claim 5 wherein said antibodies are monoclonal antibodies.

7. The method according to claim 4, wherein said binding partners are a set of aptamers.

8. The method according to claim 4, wherein said binding partners are labelled with a detectable molecule or substance.

9. The method according to claim 8, wherein said detectable molecule or substance is selected from the group consisting of a fluorescent molecule and a radioactive molecule.

10. The method according to claim 1, wherein the levels of leuko-endothelial (CD31+/41−) microparticles, pan-leukocyte (CD11a+) microparticles, lymphocyte (CD4+) microparticles, erythrocyte (CD235a+) microparticles and hepatocyte-derived (cytokeratin-18+) microparticles in the blood sample obtained from the patient are determined by flow cytometry.

11. The method according to claim 1, wherein the levels of leuko-endothelial (CD31+/41−) microparticles, pan-leukocyte (CD11a+) microparticles, lymphocyte (CD4+) microparticles, erythrocyte (CD235a+) microparticles and hepatocyte-derived (cytokeratin-18+) microparticles in the blood sample obtained from the patient are determined by an Enzyme-linked Immunosorbent Assay (ELISA) method.

12. The method according to claim 1, wherein said at least one complication is ascites.

* * * * *